United States Patent [19]

Yannalfo

[11] Patent Number: 5,727,564
[45] Date of Patent: Mar. 17, 1998

[54] SNORE REDUCING DEVICES WITH MOLAR WEDGES AND ROOF ARCH

[76] Inventor: Janine E. Yannalfo, 10 Jennifer Pl., Glen Rock, N.J. 07452

[21] Appl. No.: 725,132

[22] Filed: Oct. 2, 1996

[51] Int. Cl.$^6$ ............................................. A61F 5/37
[52] U.S. Cl. ........................ 128/846; 128/848; 128/859
[58] Field of Search ................................ 128/846, 848, 128/857, 858, 859, 860, 861, 862; 2/2; 433/6

[56] References Cited

U.S. PATENT DOCUMENTS

| | | | |
|---|---|---|---|
| 4,715,368 | 12/1987 | George | 128/859 |
| 4,901,737 | 2/1990 | Toone | 128/848 |
| 5,562,106 | 10/1996 | Heeke | 128/848 |
| 5,570,704 | 11/1996 | Buzzard | 128/848 |

Primary Examiner—Michael A. Brown
Attorney, Agent, or Firm—Kenneth P. Robinson

[57] ABSTRACT

Snore reducing device 10 includes the combination of left and right gripping portions 12 and 14 and arch section 20. Each gripping portion 12 and 14 is configured for gripping between a user's upper and lower molars and has a wedge shape which is thicker in front. Raised side edges 16 and 18 and use of thermo-deformable material for compliant shaping to the user's molar surfaces aid in providing a comfortable fit during sleep. The arch section 20 extends upward from and between the gripping portions 12 and 14. Arch section 20 is shaped to fit adjacent to upper elements of the user's mouth in contact or spaced relationship. The snore reducing devices described do not include any front portion extending between the user's incisors to inhibit air flow into or out of the mouth during sleep.

12 Claims, 2 Drawing Sheets

SNORE REDUCING DEVICES WITH MOLAR WEDGES AND ROOF ARCH

This invention relates to oral devices for reducing snoring and, more particularly, to such devices including a roof arch interconnecting molar portions, while lacking any forward portion between the user's incisors.

BACKGROUND OF THE INVENTION

Snoring is an age old problem for which a great variety of oral devices, as well as various medical and surgical procedures, have been proposed. For different reasons, such as high cost, ineffectiveness and impracticality, such proposals have provided less than a complete solution for the problem.

Examples of prior oral devices are described in U.S. Pat. Nos. 5,462,066, 5,117,816, 5,092,346, 5,056,534 and 3,434,470. Without attempting a detailed review of the specific features described in such patents, it can be observed that commonly the disclosed devices have a full mouthpiece configuration fitted to cooperate with all of a user's teeth from rear molars to front incisors. Objectives of such prior devices are typically to limit or prevent breathing through the mouth, or force the lower jaw to a forward position, while the user sleeps. It will be observed that such objectives generally necessitate that such prior devices have a full mouth construction, including a forward portion positioned between the user's incisors. Also, the forward portion may specifically be proportioned to eliminate or constrain air flow through the front of the mouth.

Thus, while many varieties and forms of oral devices for snore prevention have been proposed, it appears that no solution which is effective, safe and economical has yet been made available.

Objects of the present invention are, therefore, to provide new and improved forms of snore reducing devices and such devices providing one or more of the following advantages and characteristics:

- molar gripping portions leaving the front of the mouth unencumbered;
- molar gripping portions of wedge shape to prevent tooth-to-tooth contact between front teeth;
- an interconnecting arch portion cooperating with the roof or other upper elements of the mouth;
- construction facilitating mouth breathing; and
- low cost construction of thermo-deformable material enabling custom fitting by the user.

SUMMARY OF THE INVENTION

In accordance with the invention, a snore reducing device, removably positionable in the mouth of a user, includes the following. A left gripping portion has a wedge shape with rear thickness less than front thickness and is suitable for gripping between upper and lower molars on the left side of the user's mouth. A right gripping portion has a wedge shape with rear thickness less than front thickness and is suitable for gripping between upper and lower molars on the right side of the user's mouth. An arch section extends upward from and between the left and right gripping portions and is shaped to fit adjacent to upper elements of the user's mouth.

A typical embodiment of the invention may be constructed of thermo-deformable plastic and include left and right gripping portions which are only about one inch in length. The gripping portions may thus be gripped between a user's molars, without extending beyond the user's canines and may exclude any front portion extending between the user's incisors to inhibit air flow in and out of the mouth. The arch section may be relatively narrow and fit in contact with or closely spaced from the roof of the user's mouth.

For a better understanding of the invention, together with other and further objects, reference is made to the accompanying drawings and the scope of the invention will be pointed out in the accompanying claims.

DESCRIPTION OF THE INVENTION

Figure 1:
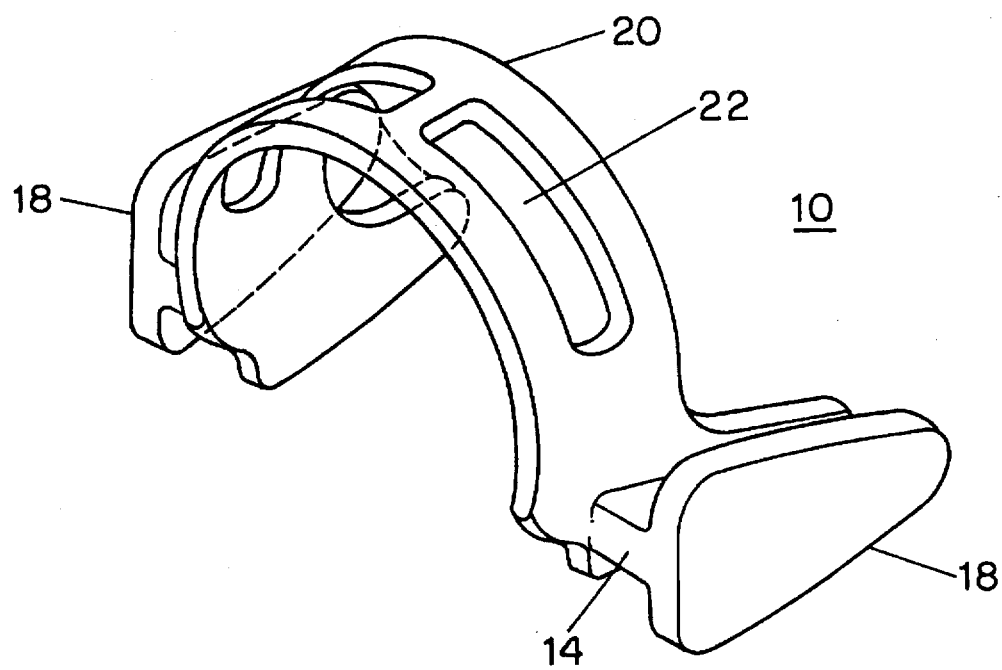
FIG. 1 is a perspective view of an embodiment of a snore reducing device in accordance with the invention.
Figure 2:
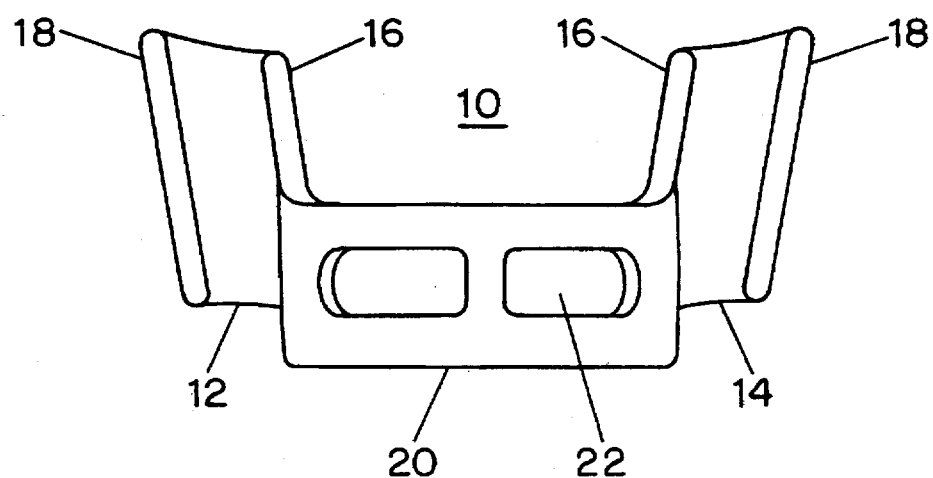
FIG. 2, FIG. 3 and FIG. 4 are respectively top, front and side views of the FIG. 1 snore reducing device.
Figure 3:
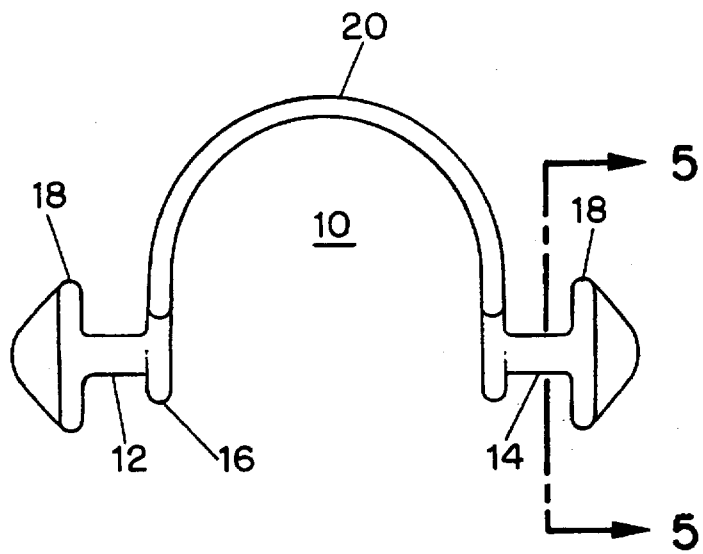
Figure 4:
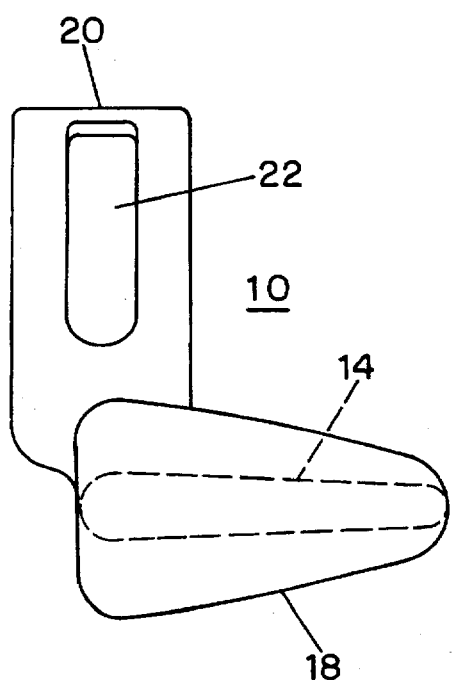

With reference to the perspective view of FIG. 1 and the top, front and side views of FIGS. 2, 3 and 4, there is illustrated an embodiment of a snore reducing device 10 in accordance with the invention. In the drawings certain dimensions have been enlarged or shown not to scale in order to show details more clearly. As shown, the device includes left and right gripping portions 12 and 14. Each gripping portion has a wedge shape with rear thickness less than front thickness, with gripping portion 12 suitable for gripping between upper and lower molars on the left side of a user's mouth and gripping portion 14 similarly suitable for gripping on the right side of the user's mouth. As shown, the left and right gripping portions may each include inner and outer raised side edges, as indicated at 16 and 18. The raised side edges 16 and 18 are effective to limit sidewards movement of the gripping portions 12 and 14 after they are positioned between a user's molars. The side edges may have any appropriate height and side profile, one example being illustrated in FIG. 4.

As shown in FIGS. 1, 2, 3 and 4, the snore reducing device also includes an arch section 20 extending upward from and between the left and right gripping portions 12 and 14. Arch section 20 is shaped to fit adjacent to upper elements of the user's mouth and, for example, may be shaped to be in contact with an element such as the roof of the user's mouth or closely spaced from upper elements of the mouth.

It has been found effective to form the left and right gripping portions 12 and 14 with integral side edges 16 and 18 of a thermo-deformable plastic material suitable for compliant shaping to fit a user's molar surfaces. Materials of this type are in common use for articles such as athletic mouth guards. When formed of a suitable material of this type, a snore reducing device 10 can be manufactured at relatively low cost. A prospective user can then purchase a non-customized unit of an appropriate size, without professional consultation or fitting. Depending upon the actual material, the device 10 can be briefly heated (in hot water, for example) before being gripped between the user's molars with the device appropriately oriented in the mouth. While heated, the left and right gripping portions 12 and 14 are deformable to enable shaping to fit the user's molar surfaces. Upon cooling, the gripping portions retain a conformal shaping to fit the biting surfaces of the user's molars. In the illustrated embodiment, arch section 20 is integrally formed of the same plastic material as the left and right gripping portions. With this construction, during the heating and self-fitting steps carried out by the user the arch section 20 is enabled to somewhat change shape, if necessary to fit the roof of the user's mouth. In other embodiments, arch section 20 may have a lower profile, so fitting of the arch is not necessary, or may be formed of a different material such as plastic or metal and attached at its ends to the left and right gripping portions to provide a complete device.

Figure 5:
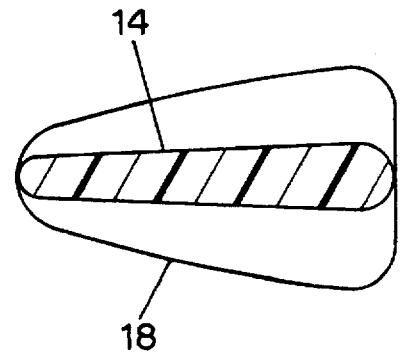
FIG. 5 is a sectional view taken along line 5—5 of FIG. 3.

Actual dimensions and shapes of portions of the snore reducing device may be changed or selected over a relatively wide range as appropriate to particular embodiments, sizes and designs. For example, the gripping portions 12 and 14 have been found effective when having a wedge shape back-to-front, with a rear thickness of the order of one-sixteenth inch and a front thickness of the order of one-eighth to three-sixteenths inch (as shown in the FIG. 5 sectional view cutting through gripping portion 14). However, those dimensions are not considered critical and may be varied as appropriate in implementation of the invention. Also, while a wedge shape is illustrated and described, in other embodiments the upper and lower surfaces of the gripping portions 12 and 14 may be parallel planar surfaces or have other selected shapes and orientations. In addition, while in FIG. 3 gripping portions 12 and 14 extend horizontally outward from the arch section 20, the device 10 may be formed with portions 12 and 14 inclined up or down side-to-side and/or rear-to-front. In FIG. 2 gripping portions 12 and 14 are shown angled inward, rear-to-front at an angle intended to be consistent with the alignment of a typical user's molars. In other embodiments, such angle may be greater or lesser or the gripping portions may be parallel, particularly when the back-to-front dimension of portions 12 and 14 is relatively small. Raised side edges 16 and 18, if included or partially included, may be of any appropriate height, thickness and shape.

As illustrated, arch section 20 is provided in a form about one-half inch wide with a thickness suitable for basic structural stability. As shown, it was found appropriate in this embodiment to remove unnecessary material from the arch section 20, resulting in openings 22. Also, as shown in the side view of FIG. 4, in this embodiment arch section 20 connects to the gripping portions 12 and 14 so that section 20 is positioned partially forward of portions 12 and 14. Actual construction, dimensions and shaping of arch section 20 are considered as matters of choice in particular embodiments and may be specified on an empirical or other basis. For example, arch section 20 may be positioned further back or further forward relative to the gripping portions 12 and 14. Arch section 20 as illustrated has a back to front width of about one-half inch, which is much smaller than its length of about two and one-half inches between left and right sections 12 and 14. As already noted, arch section 20 may be integrally formed with sections 12 and 14 or may be formed of metal or other material attached to sections 12 and 14.

Particular dimensional relationships and operational characteristics of snore reducing devices in accordance with the invention will now be considered. As noted above, prior devices intended for alleviation of snoring have typically been arranged to be what may be termed full dental devices intended to interact with the active surfaces of all of a user's teeth. Also, such prior devices have commonly extended between a user's incisors for the purpose of eliminating or controlling the flow of air in and out of the user's mouth while sleeping. The present applicant, after experience with a variety of types of previously available devices without satisfactory results, invented the present device which in trial use by a number of individuals has provided uniformly successful results in inhibiting snoring. While the theory of operation of the present devices is not necessarily fully understood by applicant, the following observations based upon experience in design and use of devices as disclosed are provided without limiting the scope or flexibility of design of snore reducing devices in accordance with the invention.

Left and right gripping portions 10 and 12 are provided for gripping between a user's molars. By providing such gripping portions with a limited rear to front dimension typically between one-half inch and one and one-half inches, the gripping portions can be positioned between the molars without extending between the user's incisors and, in the presently preferred embodiment, not even extending between the user's canines. In addition, in the presently preferred embodiment the gripping portions 12 and 14 are of wedge shape with rear thickness less than front thickness, as shown. These characteristics leave the user's front teeth separated, enabling air to pass readily into and out of the mouth and also eliminating grinding contact of teeth by the user during sleep. It is thus considered preferable that, if devices using the invention include any portion extending to the front of the mouth (as taught by various prior references), any such forward portion should not extend between the incisors in a manner inhibiting air flow.

The arch section 20, in addition to providing structural integrity to the complete device, may also contact upper elements of the user's mouth. As is known, certain prior medical or surgical procedures have sought to alleviate snoring by modifying the size of the soft palate or the uvula, or both. It is not fully understood how the arch section 20 of devices using the invention may affect a reduction in tendency to snore as a result of adjacency to such upper elements of the user's mouth. It is possible that the effectiveness of snore reducing devices using the invention derives in some degree, partially or fully, from contact or close spacing to upper elements of the mouth which is effective to generally discourage an oral configuration or alignment conducive to snoring. In any event, the combination of molar grippable portions 12 and 14 (of very limited back to front dimension or otherwise) and arch section 20, as disclosed and described, are considered to be both an effective and novel combination of elements for inclusion in snore reducing devices.

While there have been described the currently preferred embodiments of the invention, those skilled in the art will recognize that other and further modifications may be made without departing from the invention and it is intended to claim all modifications and variations as fall within the scope of the invention.

What is claimed is:

1. A snore reducing device, removably positionable in the mouth of a user, comprising:

a left gripping portion of wedge shape with rear thickness less than front thickness and suitable for gripping between upper and lower molars on the left side of the user's mouth;

a right gripping portion of wedge shape with rear thickness less than front thickness and suitable for gripping between upper and lower molars on the right side of the user's mouth; and an arch section extending upward from and between said left and right gripping portions and shaped to fit adjacent to upper elements of the user's mouth;

said left and right gripping portions each of unitary construction formed of one piece of deformable material suitable for compliant shaping to fit a user's molar surfaces to aid in position retention during use.

2. A snore reducing device as in claim 1, wherein said left and right gripping portions do not extend forward beyond the user's canines and the device does not include any front portion extending forward beyond the user's canines.

3. A snore reducing device as in claim 1, wherein said left and right gripping portions each include raised side edges.

4. A snore reducing device as in claim 1, wherein said arch section is shaped to fit in one of the following relationships: in contact with at least one upper element of the user's mouth; spaced from upper elements of the user's mouth.

5. A snore reducing device as in claim 1, wherein said the left and right gripping portions and said arch section are formed of one piece of a thermo-deformable plastic material suitable for compliant shaping to fit a user's molar surfaces.

6. A snore reducing device as in claim 1, wherein said arch section is formed of one of the following: said thermo-deformable plastic material; other plastic material; metal.

7. A snore reducing device as in claim 1, wherein said arch section has a back to front width much smaller than its length between the left and right gripping sections.

8. A snore reducing device, removably positionable in the mouth of a user, comprising:

a left gripping portion suitable for gripping between upper and lower molars on the left side of the user's mouth and extending less than one and one-half inches in a rear to front direction;

a right gripping portion suitable for gripping between upper and lower molars on the right side of the user's mouth and extending less than one and one-half inches in a rear to front direction; and an arch section extending upward from and between said left and right gripping portions and shaped to fit adjacent to upper elements of the user's mouth;

said left and right gripping portions each of unitary construction and wedge shaped with rear thickness less than front thickness and each including raised side edges, the device not including any front portion extending forward beyond the user's canines.

9. A snore reducing device as in claim 8, wherein said arch section is shaped to fit in one of the following relationships: in contact with at least one upper element of the user's mouth; spaced from upper elements of the user's mouth.

10. A snore reducing device as in claim 8, wherein said the left and right gripping portions are formed of a thermo-deformable plastic material suitable for compliant shaping to fit a user's molar surfaces and said arch section is formed of one of the following: said thermo-deformable plastic material; other plastic material; metal.

11. A snore reducing device as in claim 8, wherein said arch section has a back to front width much smaller than its length between the left and right gripping sections.

12. A snore reducing device as in claim 8, wherein said the left and right gripping portions and said arch section are formed of one piece of a thermo-deformable plastic material suitable for compliant shaping to fit a user's molar surfaces.

* * * * *